United States Patent
Clark, Jr.

[11] Patent Number: 5,836,864
[45] Date of Patent: Nov. 17, 1998

[54] PENILE LENGTHENING TRACTION DEVICE

[76] Inventor: Roland T. Clark, Jr., 22052 Islander Ln., Huntington Beach, Calif. 92646

[21] Appl. No.: 941,321

[22] Filed: Sep. 30, 1997

Related U.S. Application Data

[63] Continuation-in-part of Ser. No. 695,229, Aug. 7, 1996, abandoned.

[51] Int. Cl.[6] ........................................................ A61F 5/00
[52] U.S. Cl. ................................................................ 600/38
[58] Field of Search .......................................... 600/38–41

[56] References Cited

U.S. PATENT DOCUMENTS

| | | | |
|---|---|---|---|
| 4,753,227 | 6/1988 | Yanuck, Jr. ................................. | 600/41 |
| 5,344,396 | 9/1994 | Clark, Jr. ................................... | 600/38 |
| 5,468,211 | 11/1995 | Welch ........................................ | 600/38 |
| 5,599,275 | 2/1997 | France ....................................... | 600/38 |
| 5,624,378 | 4/1997 | Baldecchi ................................... | 600/41 |

FOREIGN PATENT DOCUMENTS 347300 8/1960 Switzerland .

Primary Examiner—John P. Lacyk
Assistant Examiner—Samuel Gilbert
Attorney, Agent, or Firm—Gene Scott of Patent Law & Venture Group

[57] ABSTRACT

A cylinder and piston device provides a sheath for securing a penis into one end of the cylinder. The piston then acts to draw a vacuum for holding the cylinder and the penis together as a unit. Once a vacuum is drawn, a means for holding the piston at a preferred position is engaged. Significant weight may be applied to the device, or the device itself may contain significant mass so as to apply a stretching force onto the penis. The device provides a means for stretching a human penis and is quickly and easily applied to the penis and removed therefrom. The device enables further weight mass to be applied to enabling a program for stretch training of the penis through the application of incremental weight additions. The device prevents lateral swelling of the penis and provides a means for locking a level of vacuum that is appropriate for holding the weight involved in the procedure and that is also comfortable to the person undergoing the weight training.

11 Claims, 4 Drawing Sheets

PENILE LENGTHENING TRACTION DEVICE

This application is a file-wrapper continuation in-part of Ser. No. 08/695,229 filed on Aug. 7, 1996 now abandoned.

BACKGROUND OF THE INVENTION

1. Field of the Invention

This invention relates generally to devices for attachment to the human body such as clamps, belts, adhesives, and suction devices. More particularly the invention relates to suction devices and specifically to an attachment device for applying a weight to a penis for lengthening and/or foreskin restoration.

2. Description of Related Art

The following art defines the present state of this field:

Stewart, U.S. Pat. No. 5,020,522 describes a compact vacuum therapy system useful in treating male impotence. The device includes a pump body, which is used for removable mounting on a tube in both storage and operational positions. The pump body includes a reciprocating piston having a circumscribing groove of a width to permit axial shifting of an O-ring sealing during movement of the piston within the pump body. The sealing device then acts as a valve to alternately seal and open a slot defined in the piston transverse to the groove during the strokes of the piston. The piston is axially oriented with the intake and the tube when the pump is mounted to the tube.

Harris, U.S. Pat. No. 5,462,514 describes an apparatus for aiding erection in men comprising an open tubular vacuum cylinder and an mounted electrically powered vacuum generating unit which mounts to an end of the cylinder and supplies a limited vacuum at a relatively high leakage rate and a vacuum controlling valve which may be used to accurately limit the vacuum.

Chaney, U.S. Pat. No. 5,195,943 shows an elastic constricting ring forming the periphery of a vacuum cylinder into tight surrounding relationship to the base of a penis, by means of a sleeve on the cylinder contiguous with the restricting ring. The sleeve is provided with a camming surface that reacts against a fixed cam element on the cylinder so that when the sleeve is rotated it is cammed axially toward the end of the vacuum cylinder in which case the restricting ring is forced off the cylinder and onto the base of the penis.

Yamanaka, U.S. Pat. No. 5,234,401 shows a device that assists in penis erection. The device contains a sealing device for accommodating a penis inside, the device also has an extracting hose connected to the device, and a pump for extracting air from within the sealing device. An expandable circular bag provided at the opening of the device and an exhaling hose for supplying air extracted by the pump into the circular bag member is used to expand the circular bag member.

Byun, U.S. Pat. No. 5,243,968 shows a massage device for speedily massaging the penis. The vacuum massage has an elongated, cylindrical receptacle having first and second ends, a deformable cone-shaped member detachably coupled to the first end of the receptacle, and having an opening provided at the central region, and a pump mechanism coupled to the second end of the receptacle. The receptacle includes a relief valve for controlling the vacuum.

Osbun et al., U.S. Pat. No. 5,421,808 describes a self-contained, battery-operated, external vacuum generator that includes an electric motor with an eccentric output shaft coupled with a reciprocating diaphragm pump in a common housing with the electric motor and batteries. A housing vacuum port is removable and mounted inline on a reversible coupler, which is received in an open end of a vacuum chamber for housing the user's flaccid penis for vacuum engorgement therapy. The reversible coupler includes a pair of concentric annular extensions for establishing a vacuum seal with the housing vacuum port. A reverse side of the coupler includes an extended coupling nipple for alternate vacuum seal attachment with tubing connected to a manual pump. The vacuum chamber tapers toward the penis introducing end to facilitate the full engorgement of the glans penis. A relative vacuum indicator on the housing permits the user to monitor the degree of negative pressure applied to the penis, which may then be adjusted with a flow control knob, mounted on the housing. The electric motor is a relatively high torque, low energy consumption motor to prevent pump stall.

Osbon et al., U.S. Pat. No. 5,244,453 shows an improved apparatus including a cylindrical vacuum chamber to cover a penis. The vacuum chamber has an open proximal end and a closed distal end. The distal end tapers to provide an integral ramp for expanding a resilient cincture band onto the outside diameter of the vacuum chamber. A vacuum connector fitting forms at the base of the ramp for evacuation of the chamber. Guard flanges help protect the fitting. The proximal end includes a cincture band groove defined about the outside diameter of the chamber, with a plurality of vent holes in the groove, pneumatically interconnecting the exterior of the chamber with its interior. A cincture band expands onto the outside diameter of the chamber and advances to it proximal end initially resides in the cincture band groove, where it covers and seals the plurality of vent holes. Once desired engorgement is achieved, the cincture band advances to the base of the penis, which simultaneously vents negative pressure within the chamber by uncovering of the vent holes. The construction of the cincture band includes a pair or semi-ellipsoidal handles and an enlarged region to be aligned with the urethra of the penis so as to reduce urethra constriction for improved seminal discharge.

The art described above is primarily for the correction of penile impedance. It does not teach a means structurally configured for connecting weight members to the penis. The prior art also does not teach a means for prevention of the swelling of the glans-penis under vacuum. The present invention fulfills these needs and provides further related advantages as described in the following summary.

SUMMARY OF THE INVENTION

The present invention teaches certain benefits in construction and use which give rise to the objectives described below.

The preferred embodiment of the present invention provides a cylinder and piston arrangement with a sheath for securing a penis into one end of the cylinder. The piston then acts to draw a vacuum for holding the cylinder and the penis together as a unit. Once a vacuum is drawn, a means for holding the piston at a preferred position is engaged. Significant weight may be applied to the device, or the device itself may contain significant mass so as to apply a stretching force onto the penis.

The primary objective of the present invention is to provide a means for stretching a human penis and to enable this stretching means to be quickly and easily applied to the penis and to be removed therefrom. Another objective of the present invention is to enable further weight mass to be applied to the attachment device enabling a program for stretch training of the penis through the application of incremental weight additions to the device. A further objective of the invention is to prevent the lateral swelling of the penis in the vacuum condition of the device. A further objective of the invention is to provide a means for locking a level of vacuum that is appropriate for holding the weight involved in the procedure and that is also comfortable to the person undergoing the weight training or conditioning. A final objective of the present invention is to prevent contraction of scar tissue. Such scar tissue may occur due to surgical procedures, due to penis lengthening or enlargement, due to Peyronies disease and other surgical and non-surgical causes.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIGURE 1A is a view similar to that of FIG. 1 but showing an alternate embodiment providing a means for locking the piston at a selected position in the cylinder;

DETAILED DESCRIPTION OF THE PREFERRED EMBODIMENT

Figure 1:
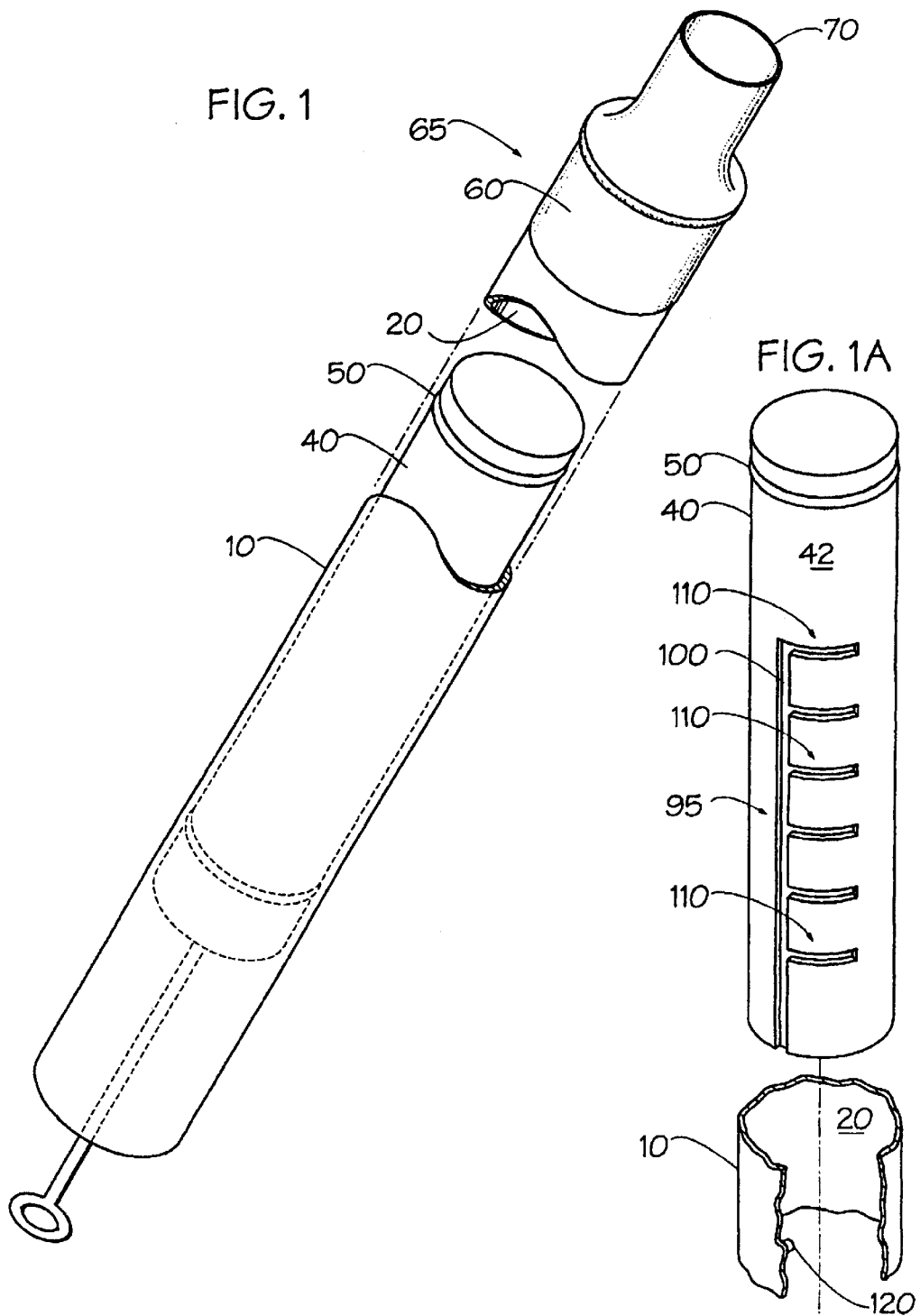
FIG. 1 is a perspective view of one preferred embodiment of the present invention with an outer side wall of a cylinder shown broken away to reveal an inner piston.
Figure 2:
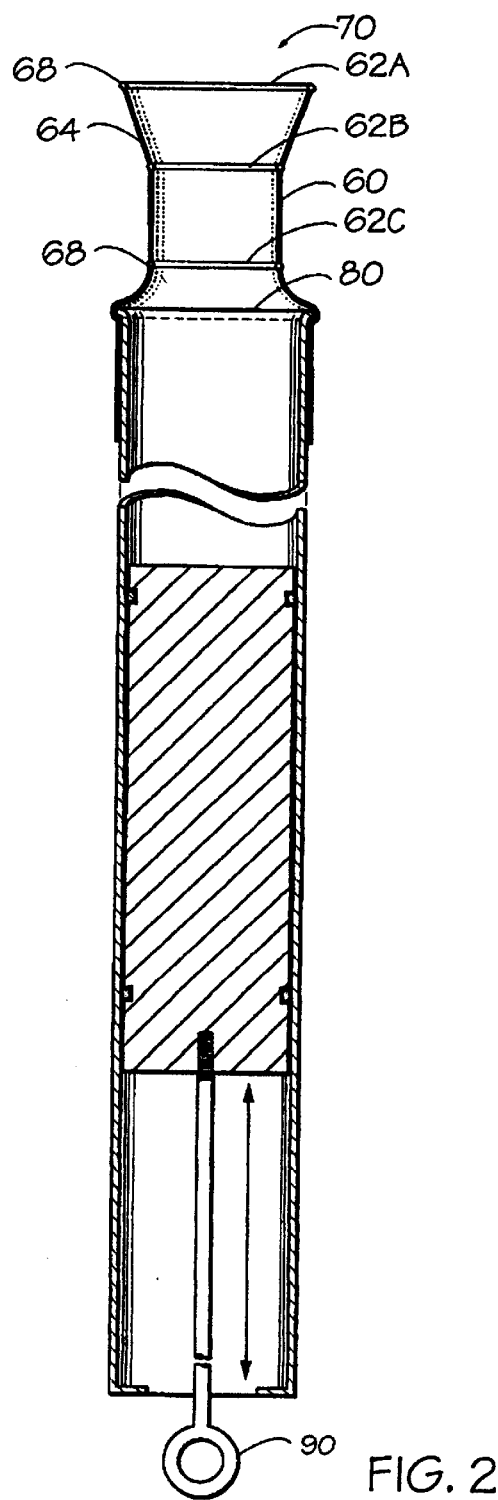
FIGS. 2 and 3 are elevational views in cross-section according to an alternate embodiment of the invention wherein the sheath of the invention provides a frustum shaped terminal portion, with FIG. 3 showing the human penis inserted into the cylinder; the penis shown before it has expanded laterally due to vacuum suction.
Figure 3:
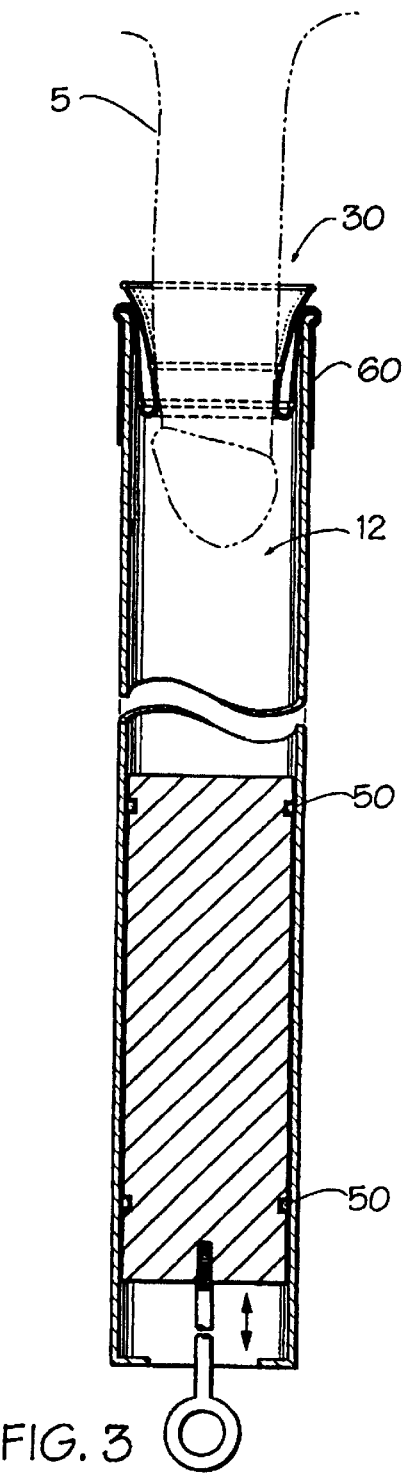

The above described drawing figures illustrate the invention, a suction device for use in forming an attachment to a human penis 5. The device, as shown in FIG. 1, includes a wall means 10, preferably a cylinder as shown in the figures, having a smooth inside wall surface 20. The wall means 10 provides an aperture 30 at one end, as shown in FIG. 3, the aperture 30 being of a size and shape as to be capable of accepting the penis 5. Preferably, the aperture 30 is round and only slightly larger than the girth of the penis 5. A piston 40 is movable within the wall means 10 and fitted therein so as to form a relatively tight sliding fit. Preferably, one or more o-rings 50, as best shown in FIGS. 2 & 3, are used to seal the piston 40 against the inside wall surface 20. A sealing means 60 is used to seal the penis within the annular wall means 10. Such a sealing means 60 is preferably a sheath which provides a proximal end 65 which when stretched around the wall means 10 adjacent to the aperture 30 forms a tight seal. This sheath (sealing means) 60 is preferably made of an elastic material such as rubber so that it is easily removed from the wall means 10. It extends distally outwardly from the wall means 10 and, in one embodiment, as shown in FIG. 1, has a distal open end 70 sized for sealing around the shaft of penis 5 when the penis 5 is inserted into the sheath 60 through open end 70. In an alternate embodiment, as shown in FIGS. 2 and 3, the open end 70 is formed as the terminus of a cone frustum 64. The sheath 60 preferably provides at least one annular bead 68 positioned for contact with the penis. The annular beads 68 help to seal the penis within the sheath 60. Alternately, the sealing means 60 may be an annular rubber boot, tape, or other means for sealing (not shown).

As best seen in FIGS. 2 and 3, the aperture 30 of the wall means 10 preferably provides an annular, outwardly directed flange 80 for improving the engagement and holding strength between the sheath 60 and the wall means 10. The piston 40 provides such mass as to enable stretch training of the penis 5. In this regard, the weight of the piston 40 and wall means 10 is preferably in the range of 1 to 40 pounds. This range of weight has been found to work advantageously in weight and condition training of the penis 5. The piston 40 further provides a means for attachment 90 of an additional weight (not shown) to it. This weight attachment means 90 may typically be a hook, an eye, or any other mechanical fastening means including magnetic attachment. In the figures the attachment means 90 is a rod threaded into the piston and providing an eye at its distal end.

As best seen in FIG. 1A the device preferably also includes a means for locking 95 of the piston 40 at a selected longitudinal position within the wall means 10. Preferably it consists of an elongated, longitudinally oriented slot 100 impressed into the surface 42 of the piston 40, with spaced apart smaller lateral slots 110. Corresponding to this slot structure 100, 110 in the piston 40, is a boss 120 extending inwardly from the inside wall surface 20 of the wall means 10. The boss 120 engages the longitudinal slot 100 so that the piston 40 may move longitudinally within the wall means 10. When the piston 40 is moved to a selected position longitudinally within the wall means 10, the piston 40 may be rotated to engage the boss 120 with one of the smaller lateral slots 110 in order to lock the piston 40 at the selected longitudinal position. Alternatively, the elongated, longitudinally oriented slot 100, with spaced apart smaller lateral slots 110, may be impressed into the inside wall surface 20, and the corresponding boss 120 may then be extending outwardly from the piston 40.

In practice, with the piston 40 positioned as in FIG. 2, the penis 5 may be inserted into the distal open end 70 of the sheath 60 as shown in FIG. 3. Preferably the distal open end 70 must be stretched over the penis 5 so as to form a tight seal around the penis shaft. The piston 40 is then drawn away from the penis as shown in FIG. 3. This action of the piston 40 pulls a vacuum in the upper end 12 of the side wall means 10, while the sheath 60 maintains a seal. Under the forces of this vacuum, the penis 5 tends to swell into contact with the inside wall surface 20 of the wall means 10 and the attachment is complete. Preferably the wall means 10 is selected to be of a size to limit the amount of lateral swelling of the penis 5. Vacuum forces hold the device to the penis 5 while the weight of the device provides a stretching force on the penis 5 generally, and may be specifically applied to a circumcised penis shaft skin for the extension thereof in extending such skin to function as foreskin.

An important aspect of the present invention is the automatic adjustment of the device when added weight is applied. To understand this, consider the device as applied to a penis 5 as described above. Assume that the piston 40 has been drawn downwardly within the cylinder 10 until just enough suction force has been applied to the penis 5 to hold the device in place on the penis 5. The piston 40 is not locked in place within the cylinder 10. Now, a further weight (not shown) is added to the piston 40, as for instance by attaching it to the attachment means 90. This new weight overcomes the existing suction force and therefore causes the piston 40 to move downwardly within the cylinder 10 until the suction force increases enough to equal the incremental force of the new weight. The piston 40 is now held in equilibrium at a new location within the cylinder 10. Notice that this establishment of a new position of the piston 40 is fully automatic.

Figure 4:
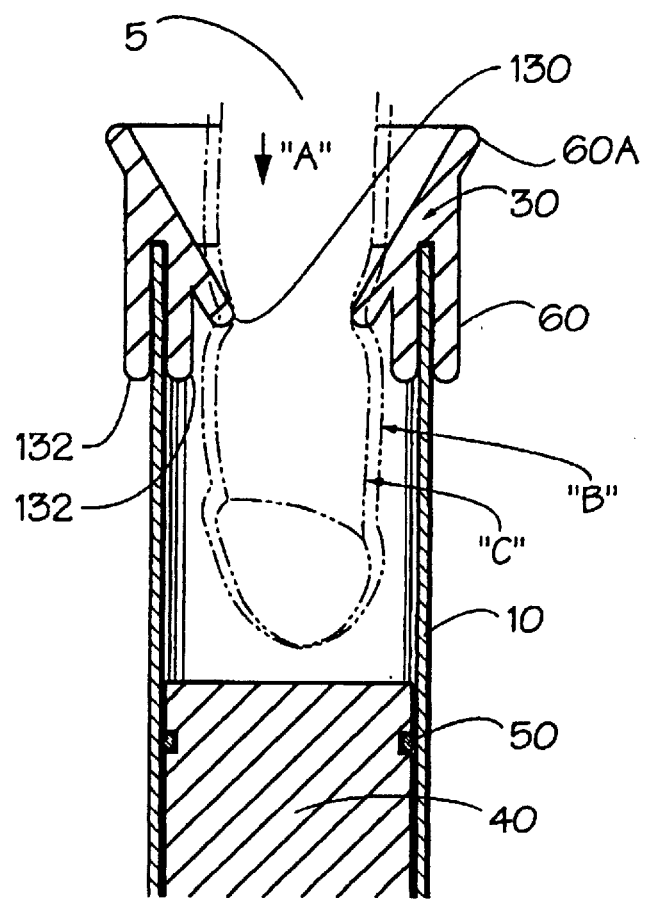
FIG. 4 is a partial section view similar to FIG. 2 showing an alternate embodiment of the device where the sheath provides an annular flexible lip adapted for sealing around a penis.

In an alternate embodiment of the invention depicted in FIG. 4, the penis sealing means 60A provides an annular lip 130 of a resilient material positioned around the aperture 30, with the annular lip 130 extending radially toward the penis 5 and is obliquely angled in the direction of penis insertion, see arrow "A" in FIG. 4, so as to form a seal around a shaft of the penis, the annular lip 130 being of such flexibility and angle as to radially deflect as the penis shaft enlarges when a vacuum is drawn in the device, the radial deflection operably improving a seal between the annular lip 130 and the shaft of the penis 5. Further, withdrawal of the penis in a direction opposite to that shown by arrow "A" causes the annular lip 130 to constrict or tighten on the shaft of the penis 5, thus resulting in a tighter seal. It should be noted that in FIG. 4 the shaft of the penis 5 is shown as having a smaller and a larger conformation with phantom lines "B" and "C" respectively. Under vacuum conditions the shaft of penis 5 expands as shown from an initial size defined by line "B" to a larger size as defined by line "C". Note that lip 130 is caused to deflect downwardly and radially outwardly in FIG. 4, in order to allow for the expansion of penis 5. It is the angle, size, position and flexible nature of the lip 130 that is the basis for successful operation of this embodiment and such is claimed. Note also the manner in which the sealing means 60A is formed so as to engage the open end of the wall means, i.e., by a double wall 132.

Figure 5:
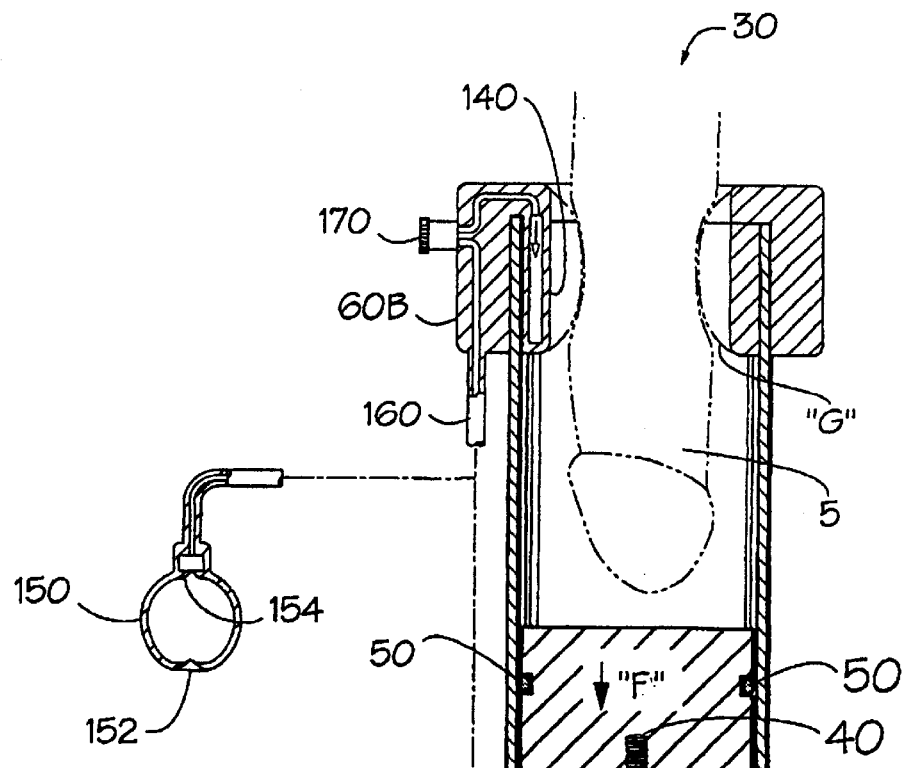
FIG. 5 is a partial sectional view similar to FIG. 2 showing the left half only as the right half is a mirror image thereof and showing details of an alternate sealing means for sealing around a penis, and showing two alternatives for inflating the sealing means; one of the alternatives being a hand pumping means, shown by numeral 150, the other being a air tube shown by numeral 160.

In a still further embodiment of the invention as shown in FIG. 5, the penis sealing means 60B provides an annular sleeve 140 made of a resilient material and positioned around the aperture 30, the annular sleeve 140 extending radially inwardly toward the penis 5 so as to form a seal around a shaft of the penis 5; the penis sealing means 60B further providing a means for inflating the annular sleeve 140 so as to radially direct the annular sleeve 140 toward the penis shaft thereby improving a seal between the annular sleeve 140 and the shaft of the penis 5.

Figure 6:
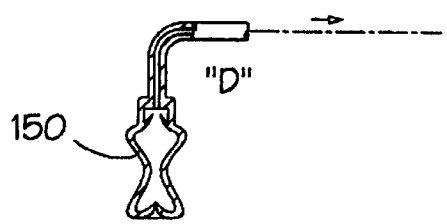
FIG. 6 is a section view of the hand pumping means shown as it is being compressed for pumping its air into the sleeve 140 shown in FIG. 5.
Figure 7:
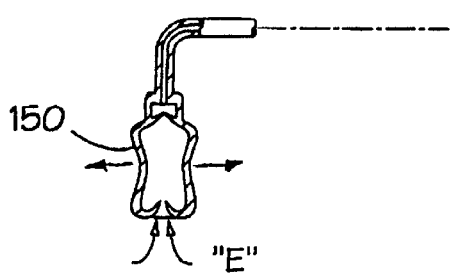
FIG. 7 is similar to FIG. 6 showing the pumping means being restored to its original shape due to its material resiliency and shape.

The inflating means, in a first embodiment shown in FIG. 5, is a manual pump means 150 having an inlet valve 152 and an outlet valve 154, the pump means 150 being in air flow communication with the annular sleeve 140 so as to force air into the sleeve for inflation it. FIG. 6 shows the pump means 150 in the process of being manually squeezed whereby forced air to move in the direction shown by arrow "D", and FIG. 7 shows the pump means 150 in the act of recovering whereby air is drawn into the pump means as shown by arrows "E". Please note the state of valves 152 and 154 in FIGS. 6 and 7. Such valves 152 and 154 may be simply annular lips that are molded integrally with the pump means 150, a bladder type air bulb.

Alternately, the inflating means comprises the wall means 10 being in air flow communication with the annular sleeve 140 such that as the piston 40 moves away from the penis 5, that is, in the direction shown by arrow "F" in FIG. 5, air is forced from the wall means into the annular sleeve 140, through tube means 160 for inflation thereof. With an enclosed chamber formed within wall means 10, the movement of piston 40 causes air entry into tube means 160. The weight exerted by piston 40 in this case pressurizes sleeve 140 causing it to expand as shown by line "G" against penis 5 for an improved seal. An auxiliary valve 170 is shown in FIG. 5. This valve is preferably a compound valve providing three functions; first, it may be set to allow air to move from the tube means 160 into the sleeve 140 for inflation thereof, second, it may be set to seal air flow into or out of the sleeve, once the sleeve is fully inflated, while allowing air to exhaust from the tube means 160 so that the piston 40 may continue to move downwardly to improve the vacuum behind it, and third, it may be set to exhaust both the sleeve and the tube means 160 when the device is to be removed from use. Such three-way valves are common in the art so that no further detailed description is provided here. An alternative to the three-way valve is to use three separate valves, whos interconnection and use for accomplishing the functions described above is well known to those of skill in the art. FIG. 5 also shows a second sliding seal 50A for sealing the shaft 90 while allowing its linear motion in either direction.

Each of the above described embodiments is able to perform the same function for fulfilling the objectives of the invention, i.e., to seal the penis securely within the device and hold the device to the penis without causing pain or blood vessel breakage in the penis structure while placing the penis in traction.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A suction device for use in forming an attachment to a penis, the device comprising:

a wall means for supporting a vacuum, provides a smooth inside wall surface, the wall means providing an aperture at one end thereof capable of accepting a human penis;

a piston movable within the wall means and fitted therein so as to form a tight sliding fit so as to operably draw a vacuum within the wall means;

a means adapted for sealing the penis in the wall means enabling exposure of the penis to the vacuum;

wherein the device provides such mass as to enable stretch training and conditioning of the penis.

2. The device of claim 1 wherein the aperture of the wall means provides an annular, outwardly directed flange, the flange being of such size as to secure the sealing means thereon.

3. The device of claim 1 wherein the piston provides a means for attachment of a weight thereto.

4. The device of claim 1 further including a means for locking the piston at a selected position in the wall means.

5. The device of claim 1 wherein the sealing means is an elastic sheath sealingly, proximally, engaged around the wall means adjacent the aperture and extending distally coaxially outwardly therefrom, the sheath having an open end sized for tightly sealing around the penis when the penis is inserted into the sheath.

6. The device of claim 5 wherein the open end of the elastic sheath is formed as a cone frustum.

7. The device of claim 5 wherein the sheath provides at least one annular bead positioned for contact with the penis.

8. The device of claim 1 wherein the penis sealing means is an annular lip of a resilient material positioned around the aperture, the annular lip extending toward the penis and obliquely angled in the direction of penis insertion so as to form a seal around a shaft of the penis, the annular lip being of such flexibility and angle as to radially deflect as the penis shaft enlarges when a vacuum is drawn in the device, the radial deflection operably improving a seal between the annular lip and the shaft of the penis.

9. The device of claim 1 wherein the penis sealing means is an annular sleeve of a resilient material positioned around the aperture, the annular sleeve extending inwardly toward the penis so as to form a seal around a shaft of the penis; the penis sealing means further providing a means for inflating the annular sleeve so as to radially direct the annular sleeve toward the penis shaft thereby improving a seal between the annular sleeve and the shaft of the penis.

10. The device of claim 9 wherein the inflating means is a manual pump means having an inlet valve and an outlet valve, the pump means being in air flow communication with the annular sleeve so as to force air into the sleeve for inflation thereof.

11. The device of claim 9 wherein the inflating means comprises the wall means being in air flow communication with the annular sleeve such that as the piston moves away from the penis, air is forced from the wall means into the annular sleeve for inflation thereof.

* * * * *